United States Patent
Choi et al.

(10) Patent No.: US 10,304,170 B2
(45) Date of Patent: May 28, 2019

(54) METHOD FOR IMAGING TARGET OBJECT WITHIN MEDIA WHICH BRING ABOUT SIMULTANEOUSLY SCATTERING AND ABERRATION

(71) Applicant: Korea University Research and Business Foundation, Seoul (KR)

(72) Inventors: Won-Shik Choi, Seoul (KR); Sung-Sam Kang, Daegu (KR)

(73) Assignee: Korea University Research and Business Foundation, Seoul (KR)

( * ) Notice: Subject to any disclaimer, the term of this patent is extended or adjusted under 35 U.S.C. 154(b) by 18 days.

(21) Appl. No.: 15/711,352

(22) Filed: Sep. 21, 2017

(65) Prior Publication Data

US 2018/0293716 A1    Oct. 11, 2018

(30) Foreign Application Priority Data

Apr. 7, 2017    (KR) .................... 10-2017-0045058

(51) Int. Cl.
*G06K 9/00*     (2006.01)
*G06T 5/00*     (2006.01)
*G01N 33/483*   (2006.01)

(52) U.S. Cl.
CPC ......... *G06T 5/006* (2013.01); *G01N 33/4833* (2013.01); *G06T 2207/20182* (2013.01); *G06T 2207/30016* (2013.01)

(58) Field of Classification Search
CPC ........................................... G06T 2207/30016
See application file for complete search history.

(56) References Cited

U.S. PATENT DOCUMENTS

| | | | |
|---|---|---|---|
| 9,541,374 B2 | 1/2017 | Brueck et al. | |
| 2008/0284869 A1* | 11/2008 | Utsugi | G06T 11/001 348/222.1 |
| 2011/0118713 A1* | 5/2011 | Raksi | A61F 9/00825 606/6 |
| 2016/0004060 A1 | 1/2016 | Simpson et al. | |
| 2018/0035883 A1* | 2/2018 | Kumar | A61B 3/1015 |

FOREIGN PATENT DOCUMENTS

| | | |
|---|---|---|
| JP | 2014-35257 A | 2/2014 |
| KR | 10-1688873 B1 | 12/2016 |

OTHER PUBLICATIONS

Zawadzki et al (NPL "Adaptive-optics optical coherence tomography for hight-resolution and high-speed 3D retinal in vivo imaging", Oct. 17, 2005 / vol. 13, No. 21 / Optics Express 8532.) (Year: 2005).*

* cited by examiner

*Primary Examiner* — Oneal R Mistry
(74) *Attorney, Agent, or Firm* — NSIP Law

(57) ABSTRACT

The present invention relates to a method for imaging a target object within media which bring about simultaneously scattering and aberration capable of imaging of deep depth and high resolution not only by maximizing an accumulation of a single aberration but also by noticeably reducing an distortion of image using simultaneous correction of the scattering and the aberration.

16 Claims, 15 Drawing Sheets
(10 of 15 Drawing Sheet(s) Filed in Color)

METHOD FOR IMAGING TARGET OBJECT WITHIN MEDIA WHICH BRING ABOUT SIMULTANEOUSLY SCATTERING AND ABERRATION

CROSS-REFERENCE TO RELATED APPLICATION(S)

This application claims the benefit under 35 USC § 119(a) of Korean Patent Application No. 10-2017-0045058 filed on Apr. 7, 2017, in the Korean Intellectual Property Office, the entire disclosure of which is incorporated herein by reference for all purposes.

TECHNICAL FIELD

The present invention relates generally to a method for imaging a target object within media which bring about simultaneously scattering and aberration. More particularly, the present invention relates to a method for imaging a target object within media which bring about simultaneously scattering and aberration capable of imaging of deep depth and high resolution by simultaneously correcting the scattering and the aberration.

BACKGROUND ART

Reaching ultimate diffraction-limit spatial resolution, which is approximately half a wavelength of a light source, is very important technology with imaging a target object embedded deep within scattering media, such as biological tissues. Multiple scattering events attenuate light waves that preserve original incidence momenta and generate multiply scattered waves, which act as strong background noise. As target depth is increased, these combined effects lead to an exponential decrease of a signal to noise ratio (SNR). Because of this, sub-micron scales of important biological reactions occurring inside living tissues have been out of reach as a consequence, and optical microscopy was unable to effectively support an investigation of the early stages of disease progression and the study of nervous systems.

When considering a target spatial resolution close to the ultimate diffraction limit, the attenuation of SNR by the multiple light scattering is not the only problem. In fact, a so-called specimen-induced aberration is an equally important issue to address. A signal wave that preserves original incidence momenta is not only attenuated in its intensity by the multiple light scattering, but its phase is also retarded due to the heterogeneity of the medium.

These phase retardations of the signal wave vary depending on a propagation angle, and the phase retardations take place for both an incident path and a returning path. These angle-dependent phase retardations cause a distortion of a reconstructed object image, and make them the main source of specimen-induced aberration. Also, they also hinder a proper accumulation of the signal wave in the image reconstruction stage and cause a further reduction in SNR in addition to that caused by multiple light scattering.

For example, the specimen-induced aberration of the typical biological tissue with thicknesses of a few scattering mean free paths (MFPs) can attenuate the single scattering intensity of the target object image by hundreds of times. This detrimental aberration effect is much more pronounced for high-resolution imaging, as waves propagating at large incidence angle retaining high-spatial frequency information tend to pass through effectively longer paths and are thus more likely to experience large phase retardation. The real challenge of these aberrations when imaging the target object in scattering media is that they are extremely difficult to identify in the presence of strong multiple light scattering.

In this regard, numerous attempts have tried to deal with either scattering or aberration individually in the past researches. The method for dealing with scattering uses a temporal gating and/or a confocal gating for the selective collection of a single-scattered wave. However, the existence of the specimen-induced aberration easily undermines these gating operations.

Using an eigenchannel to better accumulate the signal wave has been attempted, in paper of Popoff, etc. "Exploiting the Time-Reversal Operator for Adaptive Optics, Selective Focusing, and Scattering Pattern Analysis (Physical Review Letters 107, 263901 (2011))", but does not guarantee aberration compensation.

In Korean Patent number 10-1688873 "OPTICAL COHERENCE TOMOGRAPHY" which is applied by inventors of a present invention and a paper "Imaging deep within a scattering medium using collective accumulation of single-scattered waves (Nature Photonics 9, 253-258, 2015)", a method termed collective accumulation of single scattering (CASS) microscopy was proposed.

The CASS method combines both time-gated detection and spatial input-output correlation. The CASS method was used to preferentially accumulate the single-scattered wave, which is the wave scattered only once by the target object, but not at all by the medium. This has resulted in a dramatic increase of working depth such that spatial resolution of 1.5 µm can be maintained up to 11 MFPs.

For example, if the conventional method is used, the spatial resolution of 0.6 µm can be maintained only up to 8 MFPs at the same condition. However, the specimen-induced aberration in the biological tissue hinders the accumulation of the single-scattered wave. Strictly speaking, the achievable depth is even shallower than this fundamental limit by a few MFPs.

On the other hand, the method for dealing with aberration has been actively proposed in the field of adaptive optics. The aberration used to be characterized on the basis of Zernike polynomials by direct wavefront sensing or experimental feedback control. These approaches have been particularly useful for fluorescence imaging because only the aberration correction of the incident wave matters. Nevertheless, the ability to address both multiple scattering and aberrations has been limited by an insufficient number of control elements in a wavefront shaping device. The adaptive optics for the coherent imaging has proved even more difficult to implement when multiple scattering noise exists, and successful implementations have only been reported for cases with negligible multiple light scattering.

If the background noise caused by multiple light scattering is not addressed, the intensity of the single-scattered wave is less than the intensity of the background noise caused by the multiple-scattered wave. On the other hand, if aberration is not addressed, then the single-scattered wave is accumulated so ineffectively that they may not effectively compete with the multiple-scattered wave.

DISCLOSURE

Technical Problem

Accordingly, the present invention has been made keeping in mind the above problems occurring in the prior art, and an object of the present invention is to provide a method for imaging a target object within media which bring about simultaneously scattering and aberration capable of imaging of deep depth and high resolution not only by maximizing an accumulation of a single aberration but also by noticeably reducing an distortion of image using simultaneous correction of the scattering and the aberration.

Technical Solution

In order to accomplish the above object, one embodiment of the present invention provides a method for imaging a target object within media which bring about simultaneously scattering and aberration comprising the following steps: (a) obtaining a plurality of emission beams emitted from the target object in accordance with change of an incidence angle of an incidence beam; (b) constructing a time-resolved emission matrix which is composed of an incidence wave vector of the incidence beam and an emission wave vector of the emission beam; (c) re-constructing the time-resolved emission matrix to an incidence path aberration correction matrix which is composed of the incidence wave vector and a deviation between the emission wave vector and the incidence wave vector; (d) applying an incidence path aberration correction set to the incidence path aberration correction matrix, thereby calculating an optimum incidence path aberration correction set at which a total intensity of complex sum of a deviation spectrum between the emission beam and the incidence beam is maximized; (e) correcting the time-resolved emission matrix by using optimum incidence path aberration correction set; (f) re-constructing the time-resolved emission matrix corrected in the step (e) to a emission path aberration correction matrix which is composed of the emission wave vector and a deviation between the incidence wave vector and the emission wave vector; (g) applying an emission path aberration correction set to the emission path aberration correction matrix, thereby calculating an optimum emission path aberration correction set at which a total intensity of complex sum of a deviation spectrum between a reverse emission beam and a reverse incidence beam is maximized, the reverse emission beam and the reverse incidence beam have reverse phase corresponding to the emission path aberration correction matrix; (h) correcting the time-resolved emission matrix corrected in the step (e) by using the optimum emission path aberration correction set; and (i) obtaining an image by accumulating same deviation spectrum between the emission beam and the incidence beam in the time-resolved emission matrix corrected in the step (h).

Herein, the step (c) to the step (h) is repetitively executed for the corrected time-resolved emission matrix according to a pre-registered standard; and the step (i) is executed after repetitive execution of the step (c) to the step (h).

Further, the emission beam comprises a reflection beam reflected from the target object or a penetration beam penetrating the target object.

Further, a spectrum of the emission beam to which the incidence path aberration correction set is applied in the step (d) is defined by formula $$\varepsilon_{CLASS}^{(1)}(\Delta \vec{k}) = \sum_{\vec{k}^i} \varepsilon_o(\vec{k}^i + \Delta \vec{k}) e^{i\theta_i^{(1)}(\vec{k}^i)}$$

$$= \sqrt{\gamma} O(\Delta \vec{k}) \cdot \sum_{\vec{k}^i} P_i^a(\vec{k}^i) P_o^a(\vec{k}^i + \Delta \vec{k}) e^{i\theta_i^{(1)}(\vec{k}^i)} +$$

$$\sqrt{\beta} \sum_{\vec{k}^i} \varepsilon_o^M(\vec{k}^i + \Delta \vec{k}) e^{i\theta_i^{(1)}(\vec{k}^i)}$$

wherein $\theta_i^{(1)}(\vec{k}^i)$ is the incidence path aberration correction set, $P(\vec{k})$ is a complex pupil function where a subscript 'o' represents an emission path and 'i' represents an incidence path, $\gamma = \exp[-2L/l_s]$, L is a thickness of the media, ls is a scattering mean free path, $\beta$ is an average intensity of a multiple scattering wave in the emission beam, $\vec{k}^i$ is the incidence wave vector, and $\vec{k}^o$ is the emission wave vector which is $\vec{k}^o = \vec{k}^i + \Delta \vec{k}$.

Further, the deviation spectrum between the reverse emission beam and the reverse incidence beam to which the emission path aberration correction set is applied in the step (g) is defined by formula a. $\varepsilon_{CLASS}^{pc}(\Delta \vec{k}) = \sqrt{\gamma} O^{-1}(\Delta \vec{k}) \cdot \sum_{\vec{k}^o} P_o^a(\vec{k}^o)^* P_i^{(1)}(\vec{k}^o + \Delta \vec{k})^* \exp i\theta_o^{(1)}(\vec{k}^o) +$ b. $\sqrt{\beta} \sum_{\vec{k}^o} \varepsilon_o^M(\vec{k}^o + \Delta \vec{k})^* \exp[i\theta_i^{(1)}(\vec{k}^i)] \exp i\theta_0^{(1)}(\vec{k}^o)$ wherein $\theta_o^{(1)}(\vec{K}_o)$ is the emission path aberration correction set, $P(\vec{k})$ is a complex pupil function where a subscript 'o' represents an emission path and 'i' represents an incidence path, $\gamma = \exp[-2L/l_s]$, $\beta$ is an average intensity of a multiple scattering wave in the emission beam, $\vec{k}^i$ is the incidence wave vector, and $\vec{k}^o$ is the emission wave vector which is $\vec{k}^o = \vec{k}^i + \Delta \vec{k}$.

Further, the incidence path aberration correction matrix is re-constructed as type of time-resolved emission matrix after applying the optimum incidence path aberration correction set to the incidence path aberration correction matrix, thereby the time-resolved emission matrix being corrected in the step (e).

Further, the emission path correction matrix is re-constructed as type of time-resolved emission matrix after applying the optimum emission path aberration correction set to the emission path correction matrix, thereby the time-resolved emission matrix being corrected in the step (h).

Further, a number of random pattern lights with a plurality of incidence angles is incident as the incidence beam.

In order to accomplish the above object, the other embodiment of the present invention provides a method for imaging a target object within media which bring about simultaneously scattering and aberration comprising the following steps: (A) obtaining a plurality of emission beams emitted from the target object in accordance with change of an incidence angle of an incidence beam; (B) constructing a time-resolved emission matrix which is composed of an incidence wave vector of the incidence beam and an emission wave vector of the emission beam; (C) re-constructing the time-resolved emission matrix to an emission path aberration correction matrix which is composed of the emission wave vector and a deviation between the incidence wave vector and the emission wave vector; (D) applying an emission path aberration correction set to the emission path aberration correction matrix, thereby calculating an optimum emission path aberration correction set at which a total intensity of complex sum of a deviation spectrum between a reverse emission beam and a reverse incidence beam is maximized, the reverse emission beam and the reverse incidence beam have reverse phase corresponding to the emission path aberration correction matrix; (E) correcting the time-resolved emission matrix by using the optimum emission path aberration correction set; (F) re-constructing the time-resolved emission matrix corrected in the step (E) to an incidence path aberration correction matrix which is composed of the incidence wave vector and a deviation between the emission wave vector and the incidence wave vector; (G) applying an incidence path aberration correction set to the incidence path aberration correction matrix, thereby calculating an optimum incidence path aberration correction set at which a total intensity of complex sum of a deviation spectrum between the emission beam and the incidence beam is maximized; (H) correcting the time-resolved emission matrix corrected in the step (E) by using optimum incidence path aberration correction set; and (I) obtaining an image by accumulating same deviation spectrum between the emission beam and the incidence beam in the time-resolved emission matrix corrected in the step (H).

Herein, the step (C) to the step (H) is repetitively executed for the corrected time-resolved emission matrix according to a pre-registered standard; and the step (I) is executed after repetitive execution of the step (C) to the step (H).

Further, the emission beam comprises a reflection beam reflected from the target object or a penetration beam penetrating the target object.

Further, wherein a spectrum of the emission beam to which the incidence path aberration correction set is applied in the step (G) is defined by formula a. $\varepsilon_{CLASS}^{(1)}(\Delta \vec{k}) = \sum_{\vec{k}^i} \varepsilon_o(\vec{k}^i + \Delta \vec{k}) e^{i\theta_i^{(1)}(\vec{k}^i)}$ b. $\quad = \sqrt{\gamma} O(\Delta \vec{k}) \cdot \sum_{\vec{k}^i} P_i^a(\vec{k}^i) P_o^a(\vec{k}^i + \Delta \vec{k}) e^{i\theta_i^{(1)}(\vec{k}^i)} +$ $\sqrt{\beta} \sum_{\vec{k}^i} \varepsilon_o^M(\vec{k}^i + \Delta \vec{k}) e^{i\theta_i^{(1)}(\vec{k}^i)}$ wherein $\theta_i^{(1)}(\vec{k}^i)$ is the incidence path aberration correction set, $P(\vec{k})$ is a complex pupil function where a subscript 'o' represents an emission path and 'i' represents an incidence path, $\gamma = \exp[-2L/l_s]$, L is a thickness of the media, ls is a scattering mean free path, β is an average intensity of a multiple scattering wave in the emission beam, $\vec{k}^i$ is the incidence wave vector, and $\vec{k}^o$ is the emission wave vector which is $\vec{k}^o = \vec{k}^i + \Delta \vec{k}$.

Further, the deviation spectrum between the reverse emission beam and the reverse incidence beam to which the emission path aberration correction set is applied in the step (D) is defined by formula a. $\varepsilon_{CLASS}^{pc}(\Delta \vec{k}) = \sqrt{\gamma} O^{-1}(\Delta \vec{k}) \cdot \sum_{\vec{k}^o} P_o^a(\vec{k}^o)^* P_i^{(1)}(\vec{k}^o + \Delta \vec{k})^* \exp i\theta_o^{(1)}(\vec{k}^o) +$ b. $\sqrt{\beta} \sum_{\vec{k}^o} \varepsilon_o^M(\vec{k}^o + \Delta \vec{k})^* \exp[i\theta_i^{(1)}(\vec{k}^i)] \exp i\theta_0^{(1)}(\vec{k}^o)$ wherein $\theta_o^{(1)}(\vec{k}^o)$ is the emission path aberration correction set, $P(\vec{k})$ is a complex pupil function where a subscript 'o' represents an emission path and 'i' represents an incidence path, $\gamma = \exp[-2L/l_s]$, β is an average intensity of a multiple scattering wave in the emission beam, $\vec{k}^i$ is the incidence wave vector, and $\vec{k}^o$ is the emission wave vector which is $\vec{k}^o = \vec{k}^i + \Delta \vec{k}$.

Further, the incidence path aberration correction matrix is re-constructed as type of time-resolved emission matrix after applying the optimum incidence path aberration correction set to the incidence path aberration correction matrix, thereby the time-resolved emission matrix being corrected in the step (H).

Further, the emission path correction matrix is re-constructed as type of time-resolved emission matrix after applying the optimum emission path aberration correction set to the emission path correction matrix, thereby the time-resolved emission matrix being corrected in the step (E).

Further, a number of random pattern lights with a plurality of incidence angles is incident as the incidence beam.

Advantageous Effects

According to the present invention, there is provided a method for imaging a target object within media which bring about simultaneously scattering and aberration capable of imaging of deep depth and high resolution not only by maximizing an accumulation of a single aberration but also by noticeably reducing a distortion of image using simultaneous correction of the scattering and the aberration.

DESCRIPTION OF DRAWINGS

The patent or application file contains a least one drawing executed in color. Copies of this patent or patent application publication with color drawing(s) will be provided by the Office upon request and payment of the necessary fee.

MODE FOR INVENTION

Hereinbelow, exemplary embodiments of the present invention will be described in detail with reference to the accompanying drawings.

Prior to explanation of the present invention, effects of an aberration under existence of a strong multiple scattering is explained.

Figure 1:
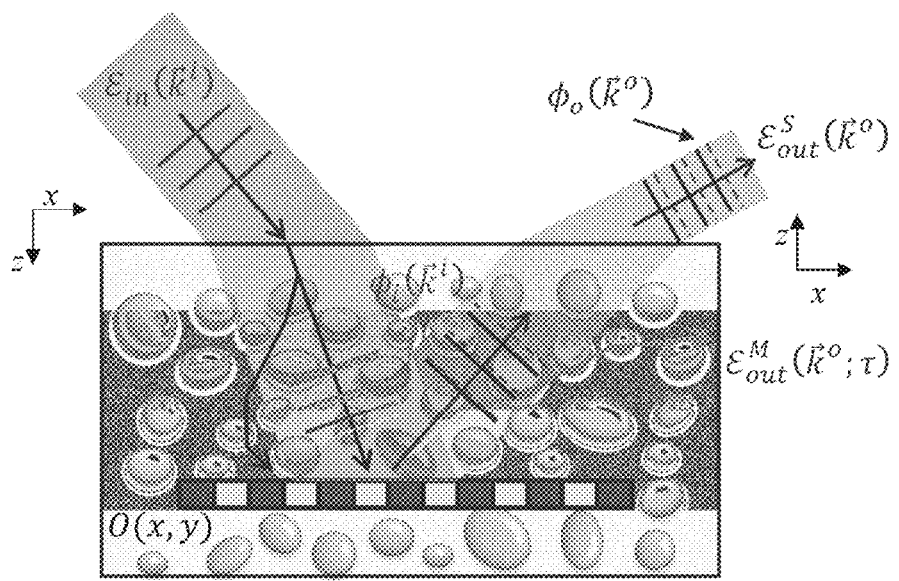
FIG. 1 shows shapes of an incidence beam and a reflection beam at a target object within media which bring about simultaneously scattering and aberration.

Referring to FIG. 1, an incidence wave (a plan wave) incident to a target object embedded in a thick scattering medium is represented as $E(x,y,z=0;\vec{k}^i)=\exp[-ik_x^i x-ik_y^i y]$. Herein, $\vec{k}^i=(k_x^i,k_y^i)$ is a transverse wave vector, that is wave vector of the incidence wave.

When the incidence wave travels through the scattering medium of thickness L, an intensity of the wave that preserves its original momentum is attenuated by a factor of $\exp(-L/ls)$, where ls is a scattering mean free path, due to multiple light scattering. Moreover, this unscattered wave undergoes a phase retardation $\phi_i(\vec{k}^i)$ depending on $\vec{k}^i$. And then, the unscattered wave reflected by the target object whose amplitude reflectance may be described by an object function $O(x,y)$, and gains the transverse wave vector $\Delta\vec{k}$ driven by an object spectrum $O(\Delta\vec{k})$, which is a Fourier transform of the object function. The wave vector of an emission wave, that is a reflection wave reflected from the target object, as shown in FIG. 1, can be represented as $\vec{k}^o=\vec{k}^i+\Delta\vec{k}$, and the reflection wave is attenuated by the multiple scattering process and also experiences the additional aberration described by an phase retardation $\phi_o(\vec{k}^o)$ depending on an incidence angle of the incidence wave. Therefore, an angular spectrum of the reflection wave having a flight time of $\tau_0=2L/c$ can be represented as [Formula 1]

$$\varepsilon_o(\vec{k}^o,\vec{k}^i)=\sqrt{\gamma}P_o^a(\vec{k}^i+\Delta\vec{k})O(\Delta\vec{k})P_i^a(\vec{k}^i)+\sqrt{\beta}\varepsilon_o^M(\vec{k}^i+\Delta\vec{k};\tau_0) \quad [\text{Formula 1}]$$

In [Formula 1], a first term on a right-hand side a single-scattered wave, a second term is a multiple-scattered wave that have same wave vector and flight time as those of the single-scattered wave. The remaining multiple-scattered wave can be ruled out by time-gated detection.)

In [Formula 1], $P_i^a(\vec{k}^i)=P(\vec{k}^i)\exp[-\phi_i(\vec{k}^i)]$ and $P_o^a(\vec{k}^o)=P(\vec{k}^o)\exp[-\phi_o(\vec{k}^o)]$ are complex pupil functions for an incidence path and a reflection path, respectively, and $P(\vec{k})$ is a pupil function of an ideal objective lens. For the ideal objective lens, $P(\vec{k})=1$ for $|\vec{k}|\leq k_0\alpha$ or is satisfied, where $\alpha$ is numerical aperture of the objective lens and $k_0$ is a magnitude of the wave vector in free space, and otherwise $P(\vec{k})=0$.

A factor $\gamma=\exp[-2L/l_s]$ describes an intensity attenuation of the single-scattered wave for the round trip through the target object. $\beta$ is an average intensity of the multiple-scattered wave detected by a camera, which is determined by an imaging optics, a time-gating window, and an optical properties of the scattering medium.

The single-scattered wave, which contains information of the target object, can be obscured by the strong multiple-scattered wave, because $\gamma/\beta$ is reduced with increasing the depth of the target object.

In the above mentioned CASS method, effects of the strong multiple scattering was eliminated by the accumulation of the single-scattered wave. In the CASS method, spatial frequency spectra of the reflection wave for $N_m$ different wave vectors of the incidence wave was measured. In order to preferentially accumulate the single-scattered wave, the reflection waves that originate from the same object spectrum $\Delta\vec{k}$ are coherently added. This can be represented as [Formula 2].

$$\varepsilon_{CASS}(\Delta\vec{k}) = \sum_{\vec{k}^i}\varepsilon_0(\vec{k}^i+\Delta\vec{k}) \quad [\text{Formula 2}]$$
$$= \sqrt{\gamma}O(\Delta\vec{k})\cdot\sum_{\vec{k}^i}P_i^a(\vec{k}^i)P_o^a(\vec{k}^i+\Delta\vec{k})+$$
$$\sqrt{\beta}\sum_{\vec{k}^i}\varepsilon_o^M(\vec{k}^i+\Delta\vec{k})$$

Here, a summation at a first term on a right-hand side of [Formula 2] is a cross-correlation between the complex pupil functions of the incidence path and the reflection path, and amplifies the object function in proportion to $N_m$. In contrast, an amplitude of the multiple-scattered wave grows in proportion to $\sqrt{N_m}$. Therefore, a signal to noise ratio of the intensity is increased from $\gamma/\beta$ to $(\gamma/\beta)N_m$, and the single scattering intensity can outgrow that of the multiple scattering when $N_m>\beta/\gamma$.

However, existence of the aberration significantly undermines the accumulation of the single scattering signal. This is because the cross-correlation of the complex-valued pupil functions is always smaller than that in the aberration-free case due to an inequality. To quantify the effect of the aberration, a parameter $\eta$ that describes a ratio between a total accumulated single-scattering intensity with the aberration and that without the aberration is defined as [Formula 3].

$$\eta = \frac{\left\|\sum_{\vec{k}^i} P_i^a(\vec{k}^i)P_o^a(\vec{k}^i+\Delta\vec{k})\right\|^2_{\Delta\vec{k}}}{\left\|\sum_{\vec{k}^i} P(\vec{k}^i)P(\vec{k}^i+\Delta\vec{k})\right\|^2_{\Delta\vec{k}}} \leq 1 \quad [\text{Formula 3}]$$

Here, $\|f(\Delta\vec{k})\|^2_{\Delta\vec{k}}$ represents summation of an absolute square of for all possible $\Delta\vec{k}$. Due to the aberration, the signal to noise ratio of the imaging according the CASS method is reduced from $(\gamma/\beta)N_m$ to $(\eta\gamma/\beta)N_m$. This suggests that the target object may not be resolvable even if $N_m>\beta/\gamma$.

As a point of reference for the effect of the aberration, a Strehl ratio S, a ratio of a peak intensity of a point-spread-function with and without aberration is used in the present invention. Both S and $\eta$ are attenuated with the increase of the aberration, but in general $S<\eta$. Typical adaptive optics can deal with the aberration corresponding to $S\geq 0.1$. However, the degree of the aberration according to the present invention was so severe that S is two orders of magnitude smaller than that the conventional adaptive optics can handle. In addition to the reduction in signal intensity, the cross-correlation adds $\Delta\vec{k}$-dependent phase retardation to the measured object function, thereby distorting a reconstructed object image.

Figure 2A:
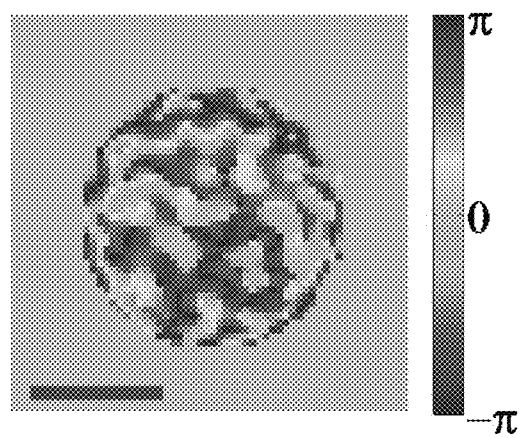
FIGS. 2A to 2C show an experimental result for verifying effects of the aberration.
Figure 2B:
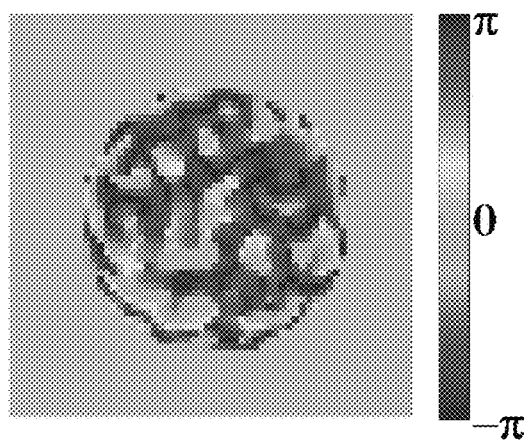
Figure 2C:
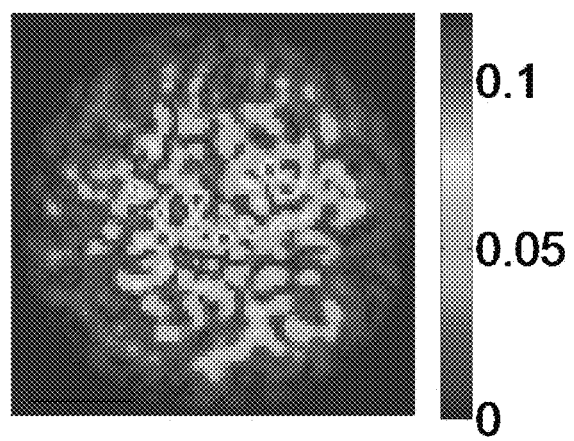

FIGS. 2A to 2C show an experimental result for verifying effects of the aberration. Referring to FIGS. 2A to 2C, a simulation is performed for the condition that $\beta=20\gamma$ and $N_m=1245$. The size of a field of view (FOV) which is used in the simulation is $20\times 20$ $\mu m^2$. Also, arbitrary aberrations $\phi_i(\vec{k}^i)$ and $\phi_o(\vec{k}^o)$ as shown in FIGS. 2A and 2B, respectively, which led to $\eta=1/400$ and $S=1/2600$, are applied.

An amplitude of a cross-correlation map of these two complex pupil functions was well below unity, as shown in FIG. 2C, suggesting that the accumulation of the single scattering would be compromised.

Figure 3A:
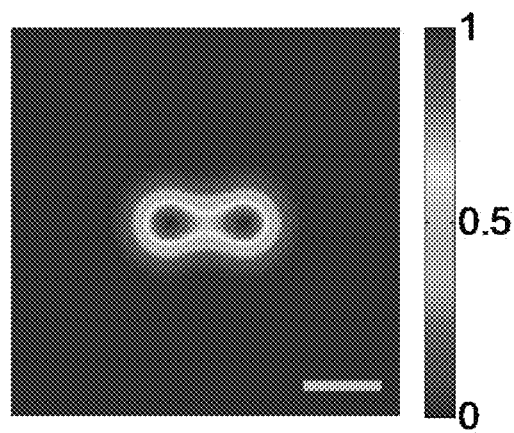
FIGS. 3A to 3D show an example of an image obtained by a conventional CASS method.
Figure 3B:
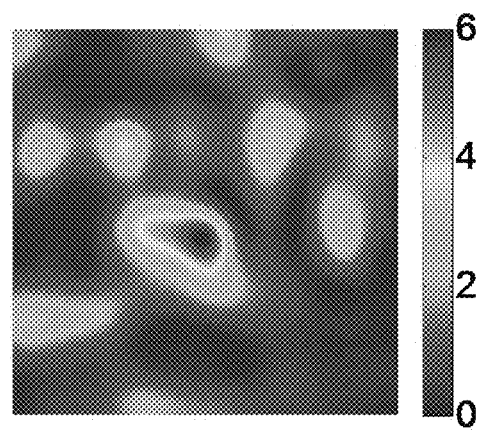
Figure 3C:
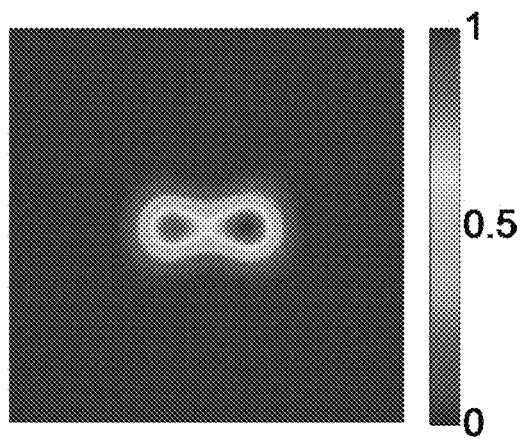
Figure 3D:
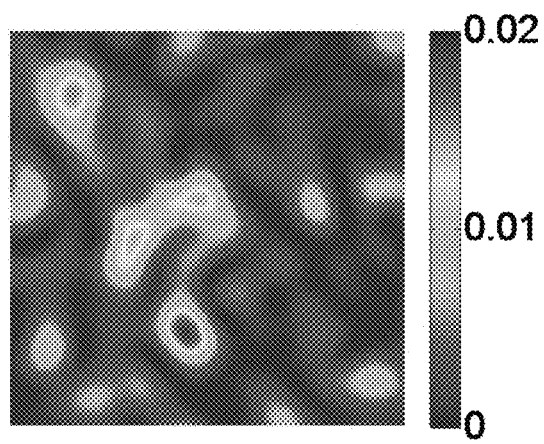

FIG. 3C and show the image of the CASS method without the aberration and the image of the CASS method with the aberration, respectively, in the absence of the multiple scattering.

As shown in FIGS. 3A to 3D, the simultaneous presence of the scattering and the aberration (referring to FIG. 3B) makes it even more difficult to distinguish between two particles than in the aberration-only case because, not only the single-scattered wave is improperly accumulated, but also the single-scattered wave are concealed by the multiple-scattered wave.

Hereinafter, referring to FIGS. 4 and 5, the method for imaging the target object within media which bring about simultaneously the scattering and the aberration is explained in detail. In the present invention, as shown in FIGS. 4 and 5, after the incidence wave is incident into the medium and passes through the incidence path, the wave is reflected from the target object and passes through the reflection path along the medium, thereby being imaged, that is, the case of reflection, as an example.

Figure 4:
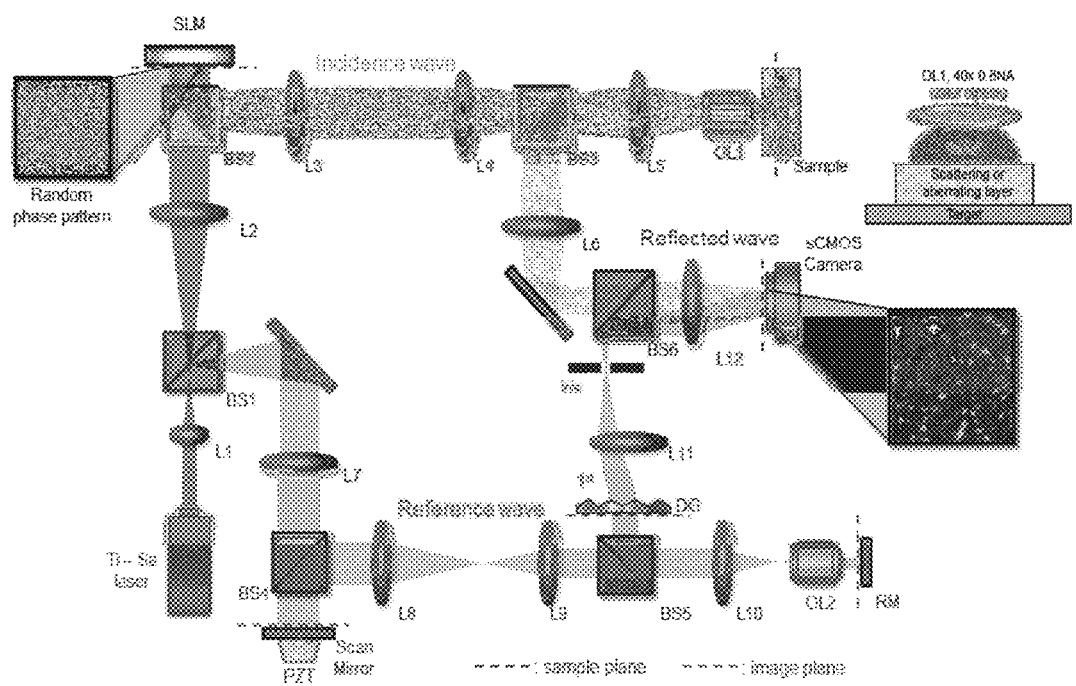
FIG. 4 shows a schematic diagram of an experimental setup for performing a method for imaging according to the present invention.
Figure 5:
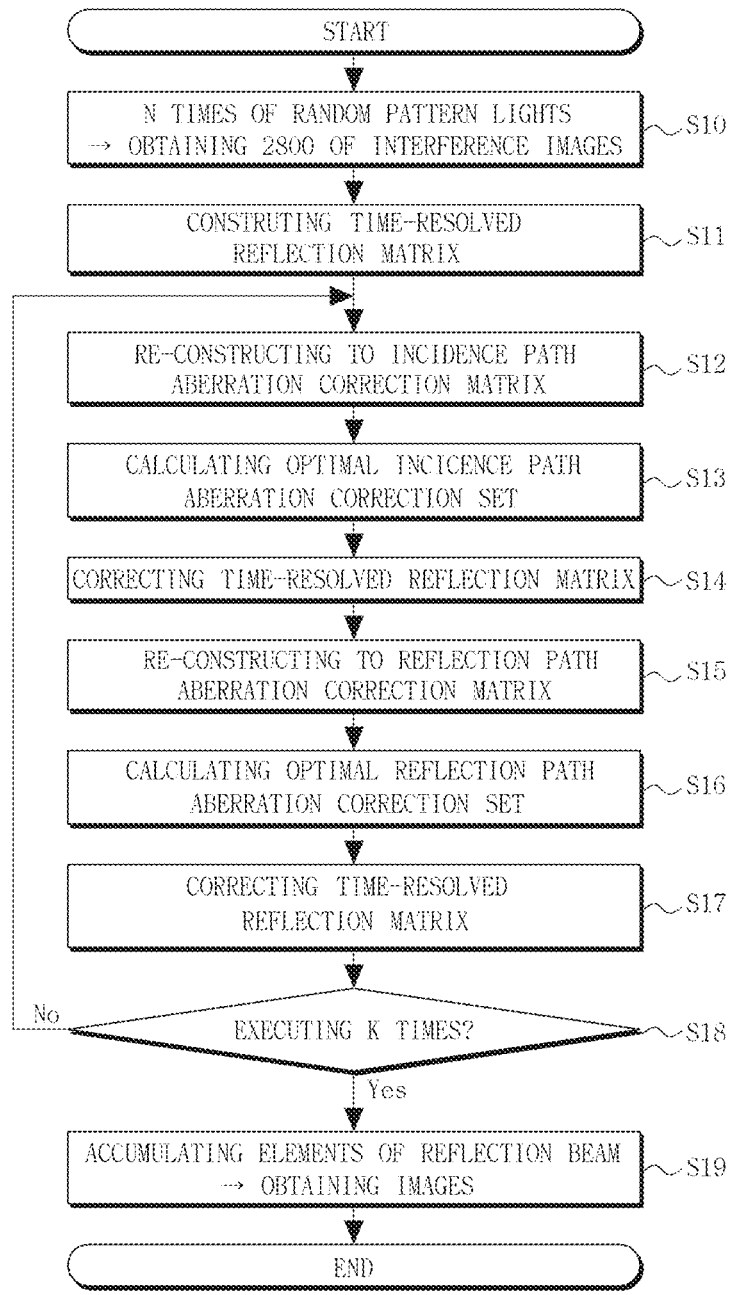
FIG. 5 explains a method for imaging a target object within media which bring about simultaneously scattering and aberration according to the present invention.

FIG. 4 shows a schematic diagram of an experimental setup for performing the method for imaging according to the present invention. Referring to FIG. 4, an interference microscope is applied. The interference microscope uses a femtosecond laser with center wavelength 800 nm and bandwidth 30 nm, and a Mach-Zhender interferometer.

The light from the laser passes through a lens L1, and is divided into a sample beam and a reference beam at a beam splitter B1. A spatial light modulator is disposed in the path of the sample beam, and adjusts a pattern of light incident to a sample, that is, adjusts an incidence angle. As one example according to the present invention, by writing 2800 random patterns on the spatial light modulator, the incidence beam incident into the sample is generated.

The incidence beam of the random pattern passing through the spatial light modulator (hereinafter, it is defined as 'random pattern light') is incident into the sample via 4-f imaging system. And, the reflection beam which reflected from the sample after passing through the medium goes to the camera via the 4-f imaging system. In the process as mentioned above, the reflection beam reflected from the sample through a beam splitter BS6 meets the reference beam and then an interference beam is generated by interference between the reflection beam and the reference beam, thereby an interference image is obtained by the camera. Herein, a beam splitter BS3 and lenses L2, L3, L4, L5, and L6 are arranged at a light path of the sample beam and the reflection beam.

Meanwhile, a diffraction grid is arranged at the light path of the reference beam, and a first diffraction beam is filtered out by diffraction grid, then the first diffraction beam generates an off-axis hologram with the reflection beam reflected from the sample through the BS6. Herein, a scan mirror is arranged at the light path of the reference beam, and can control the length of the light path of the reference beam. A product with a coherence distance of roughly 10 µm is applied as the femtosecond laser used as one example of the present invention. That is, when a difference of path length between the sample beam and the reference beam is within the coherence distance, an interference pattern is generated, and a time-resolved complex image of the reflection beam can be obtained by selecting an interference component through a Fourier transform.

Herein, beam splitters BS3, BS4, BS5 and lenses L2, L3, L4, L5, L6, L7, L8, L9, L10, L11, L12 are arranged at the light path of the sample beam, the reflection beam and the reference beam.

FIG. 5 explains a method for imaging a target object within media which bring about simultaneously scattering and aberration according to the present invention. The method in FIG. 5 is performed using the experimental setup in FIG. 4, as an example.

Firstly, the plurality of the reflection beams which are reflected from the target object are obtained in accordance with change of the incidence angle of the incidence beam. In the present invention, 2800 of the interference images are obtained using n times of the random pattern lights, e.g. 2800 times of the random pattern lights which is composed of the plurality of the incidence beams through the spatial light modulator, as an example S10. Herein, for obtaining the incidence beam, a mirror is arranged at the sample plane, and the complex images for the incidence beams are measured using 2800 of the random pattern lights which are the same as measuring the sample.

Figure 6A:
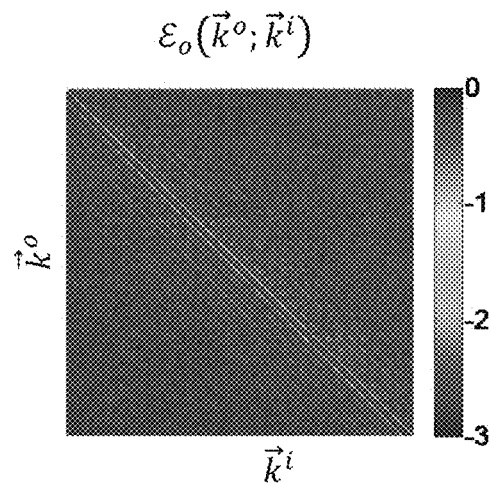
FIGS. 6A to 6C and FIGS. 7A and 7B show each matrix and each aberration correction set in a method for imaging a target object within media which bring about simultaneously scattering and aberration according to the present invention.
Figure 6B:
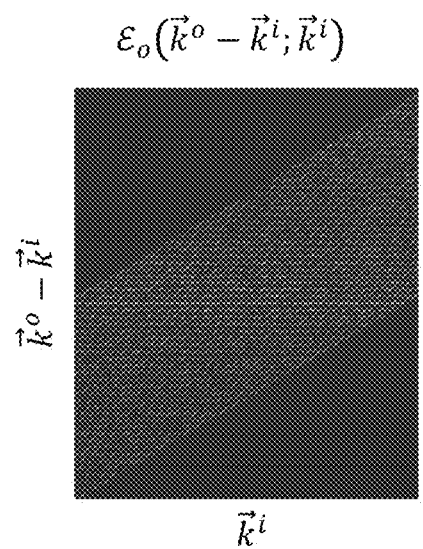

And then, by using the incidence beams measured from the mirror and the reflection beams measured from the sample, a time-resolved reflection matrix is constructed, as shown in FIG. 6A. Herein, the time-resolved reflection matrix is composed of a wave vector of the incidence beam, that is an incidence wave vector $\vec{k}^i$, and a wave vector of the reflection beam, that is a reflection waver vector $\vec{k}^o$.

And then, the time-resolved reflection matrix is re-constructed to an incidence path aberration correction matrix. The incidence path aberration correction matrix is composed of the incidence wave vector and a deviation between the reflection wave vector and the incidence wave vector.

And then, an incidence path aberration correction set $\theta_i^{(1)}(\vec{k}^i)$ is applied to the incidence path aberration correction matrix, thereby an optimum incidence path aberration correction set at which a total intensity of complex sum of a deviation spectrum $\Delta\vec{k}$· between the reflection beam and the incidence beam is maximized is calculated S13.

As such, if the time-resolved reflection matrix is corrected by using the calculated optimum incidence path aberration correction set, the aberration which is caused at the incidence path can be corrected.

Hereinafter, the correction process of the aberration which is generated at the incidence path is theoretically explained.

Firstly, the aberration which is caused at the incidence path is defined as $\phi_i(\vec{k}^i)$, and the incidence path aberration correction set for correcting the aberration is defined as $\theta_i(\vec{k}^i)$, as mentioned above.

If an arbitrary incidence path aberration correction set $\theta_i^{(1)}(\vec{k}^i)$ is applied to the deviation spectrum $\Delta\vec{k}$· between the reflection beam and the incidence beam, it can be defined by [Formula 4]. Herein, [Formula 4] can be induced by [Formula 2], thus the detailed explanation is omitted.

$$\varepsilon_{CLASS}^{(1)}(\Delta\vec{k}) = \sum_{\vec{k}^i} \varepsilon_o(\vec{k}^i + \Delta\vec{k})e^{i\theta_i^{(1)}(\vec{k}^i)} \quad [\text{Formula 4}]$$

$$= \sqrt{\gamma}\, O(\Delta\vec{k}) \cdot \sum_{\vec{k}^i} P_i^a(\vec{k}^i) P_o^a(\vec{k}^i + \Delta\vec{k})e^{i\theta_i^{(1)}(\vec{k}^i)} +$$

$$\sqrt{\beta} \sum_{\vec{k}^i} \varepsilon_o^M(\vec{k}^i + \Delta\vec{k})e^{i\theta_i^{(1)}(\vec{k}^i)}$$

And then, a set of $\theta_i^{(1)}(\vec{k}^i)$ at which the total intensity of complex sum of deviation spectrum $\Delta\vec{k}$ between the reflection beam and the incidence beam is maximized is calculated through [Formula 5], thereby the optimum incidence path aberration correction set is calculated.

$$\max_{\theta_i^{(1)}(\vec{k}^i)} \sum_{\Delta\vec{k}} |\varepsilon_{CLASS}^{(1)}(\Delta\vec{k})|^2 \quad \text{[Formula 5]}$$

In [Formula 5], while an individual $\theta_i^{(1)}(\vec{k}^i)$ is changed from 0 to $2\pi$, a particular value of $\theta_i^{(1)}(\vec{k}^i)$ at which the total intensity of complex sum of the deviation spectrum between the reflection beam and the incidence beam is maximized is fined as the optimum incidence path aberration correction set.

It is important to note that mainly the single-scattered waves take part in the above process and the multiple-scattered waves play little role. The maps of multiple-scattered waves taken at different incidence angles are uncorrelated with respect to one another, and remained so even after multiplying the phase corrections. Therefore, the maximization process of the total intensity of the spectrum of the reflection beam is almost exclusively due to the aberration correction of the single-scattered waves.

Figure 6C:
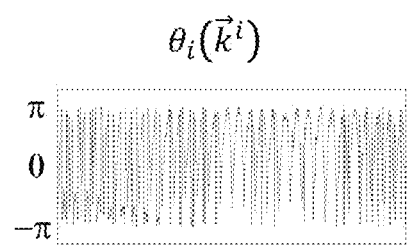

Referring to FIGS. 5 and 6C again, FIG. 6C shows the optimum incidence path aberration correction set calculated through the above process. Herein, in the present invention, the incidence path aberration correction matrix is re-constructed to time-resolved reflection matrix after the optimum incidence path aberration correction set is applied to the incidence path aberration correction matrix, thereby the aberration of the incidence path of the time-resolved reflection matrix is corrected, as an example. That this time, the optimum incidence path aberration correction set is applied to each columns of the incidence path aberration correction matrix, a same optimum incidence path aberration correction value is applied to one column.

Figure 7A:
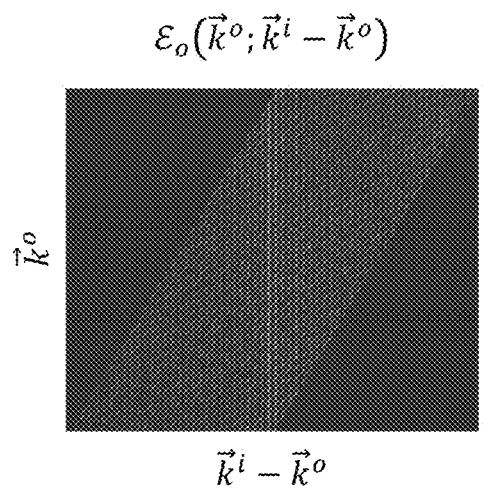

As mentioned above, when the aberration of the incidence path of the time-resolved reflection matrix is corrected, the time-resolved reflection matrix is re-constructed to a reflection path aberration correction matrix S16. Herein, the reflection path aberration correction matrix is composed of the reflection wave vector and a deviation between the incidence wave vector and the reflection wave vector, as shown in FIG. 7A.

In more detail, the reflection path aberration correction matrix represents the change of the incidence beam according to the reflection beam, and it is assumed that the reflection beam is incident into the target object as the incidence beam $-\vec{k}^o$, and the incidence beam is detected as the reflection beam $-\vec{k}^i = -(\vec{k}^o - \Delta\vec{k})$. Though the above phase conjugation, if an arbitrary reflection path aberration correction set $\vec{\theta}_o^{(1)}(\vec{k}^o)$ is applied to a deviation spectrum between the reverse incidence beam and the reverse reflection beam having reverse phase corresponding to the reflection path aberration correction matrix, it can be described by [Formula 6]

$$\varepsilon_{CLASS}^{pc}(\Delta\vec{k}) = \quad \text{[Formula 6]}$$

$$\sqrt{\gamma} O^{-1}(\Delta\vec{k}) \cdot \sum_{\vec{k}^o} P_o^a(\vec{k}^o)^* P_i^{(1)}(\vec{k}^o + \Delta\vec{k})^* \exp i\theta_o^{(1)}(\vec{k}^o) +$$

$$\sqrt{\beta} \sum_{\vec{k}^o} \varepsilon_o^M(\vec{k}^o + \Delta\vec{k})^* \exp[i\theta_i^{(1)}(\vec{k}^i)] \exp i\theta_0^{(1)}(\vec{k}^o)$$

And then, similar to [Formula 5], $\vec{\theta}_o^{(1)}(\vec{k}^o)$ at which the total intensity of complex sum of deviation spectrum between the reverse incidence beam and the reverse reflection beam is maximized is calculated, thereby an optimum reflection path aberration correction set is calculated S16.

And then, the time-resolved reflection matrix is corrected again by using the optimum reflection path aberration correction set S17, the reflection path aberration correction matrix is re-constructed to the time-resolved reflection matrix after the optimum reflection path aberration correction set is applied to the reflection path aberration correction matrix, thereby the time-resolved reflection matrix is corrected, as an example. Herein, the optimum reflection path aberration correction set is applied to each rows of the reflection path aberration correction matrix, a same optimum reflection path aberration correction value is applied to one row.

Figure 7B:
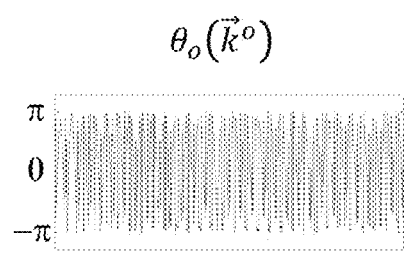

Herein, in the present invention, the above mentioned aberration correction process of the incidence path and aberration correction process of the reflection path, that is the step S12 to the step S17 are repetitively executed according to a pre-registered standard, as an example. In FIG. 5, the steps are repetitively executed a pre-registered number of times, such as k times, as an example, but the steps can be repetitively executed until the values of the optimum incidence path aberration correction set and/or the optimum reflection path aberration correction set in FIG. 6C and FIG. 7B, respectively, come close to '0'.

When the aberration correction is finished through the above process, a final image is obtained by accumulating same deviation spectrum between the emission beam and the incidence beam in the time-resolved reflection matrix S19. Herein, the obtaining image by accumulating elements of the reflection beam is the same as the above mentioned CASS method. That is, the effect caused by the multi-scattering can be eliminated through the accumulating process.

Hereinafter, referring to FIGS. 8A and 8B, FIGS. 9A to 9C, and FIGS. 10A and 10B, experimental result for explaining an effectiveness of the method for imaging according to the present invention is explained.

Figure 8A:
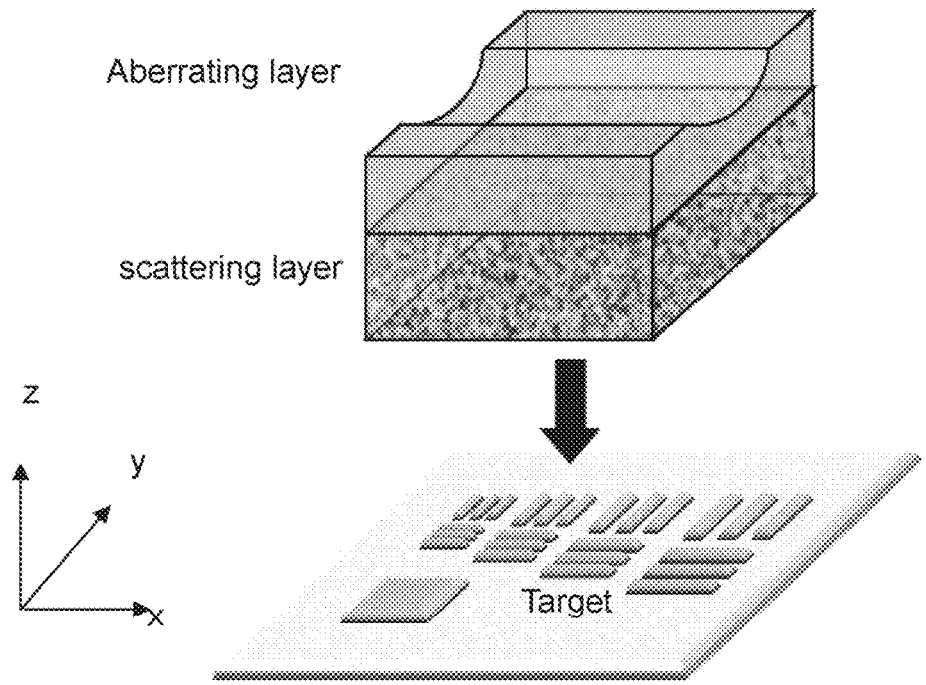
FIGS. 8A and 8B, FIGS. 9A to 9C, and FIGS. 10A and 10B explain effects of a method for imaging a target object within media which bring about simultaneously scattering and aberration according to the present invention.

As shown in FIG. 8A, an asymmetric aberration layer featuring a cylindrical groove along the y direction with a radius of curvature of 6.0 mm is prepared. Because of a refractive index mismatch between the aberration layer and an immersion medium (water, n=1.33), the cylindrical groove causes asymmetric aberrations such as astigmatisms. A $71_s$-thick scattering layer was placed underneath the aberration layer. This arrangement allowed aberration and scattering to be controlled independently.

And, a target object which is coated by gold is placed under the aberration layer and the scattering layer. Finest lines of the gold-coated target object have a separation of 600 nm. To cover all the orthogonal free modes determined by the illumination area of 30×30 μm² and a spatial frequency bandwidth corresponding to 0.8 NA, the random pattern lights numbering 2,800 were illuminated thereby the time-resolved reflection matrix is constructed, as shown in FIG. 9A.

Figure 9A:
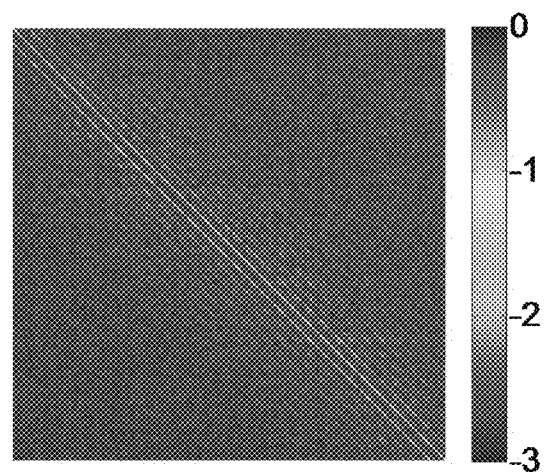
Figure 9B:
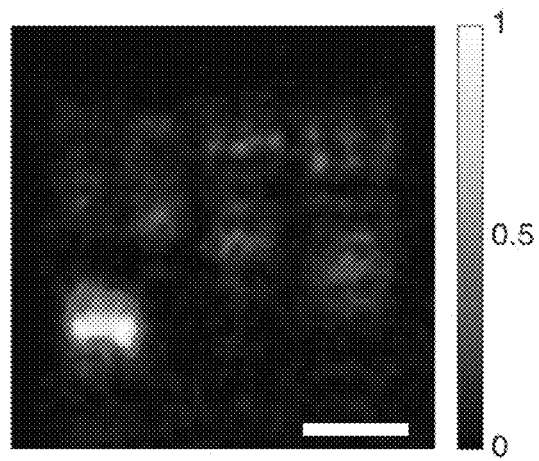

And then, by using the time-resolved reflection matrix in FIG. 9A, the images are generated by the CASS method and the method for imaging according to the present invention, respectively. As shown in FIG. 9B, in CASS method, it is difficult to distinguish the gold-coated target because of their extremely-low resolution due to the aberration. On the other hand, in the method for imaging according to the present invention, the distinction of the target is clear.

Figure 8B:
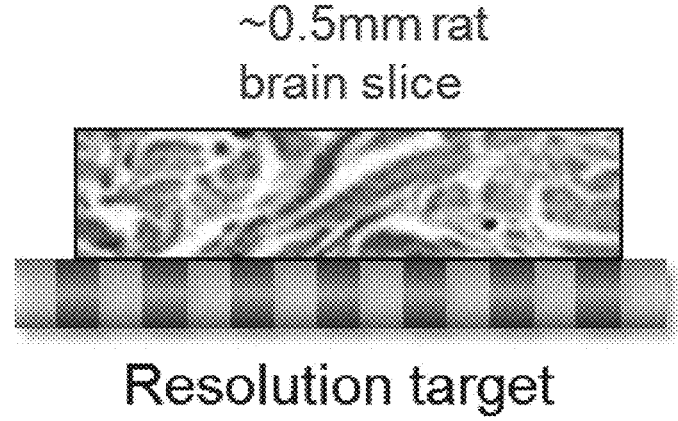
Figure 10A:
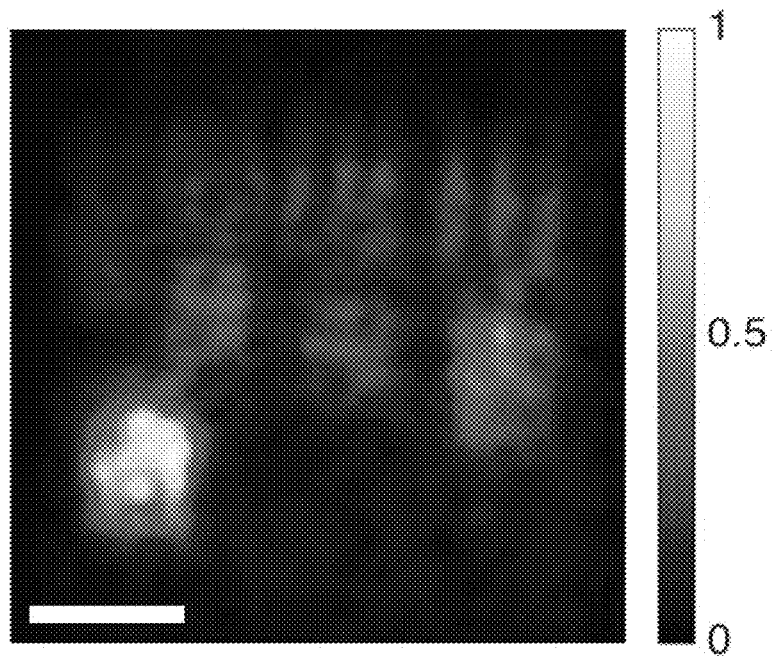
Figure 10B:
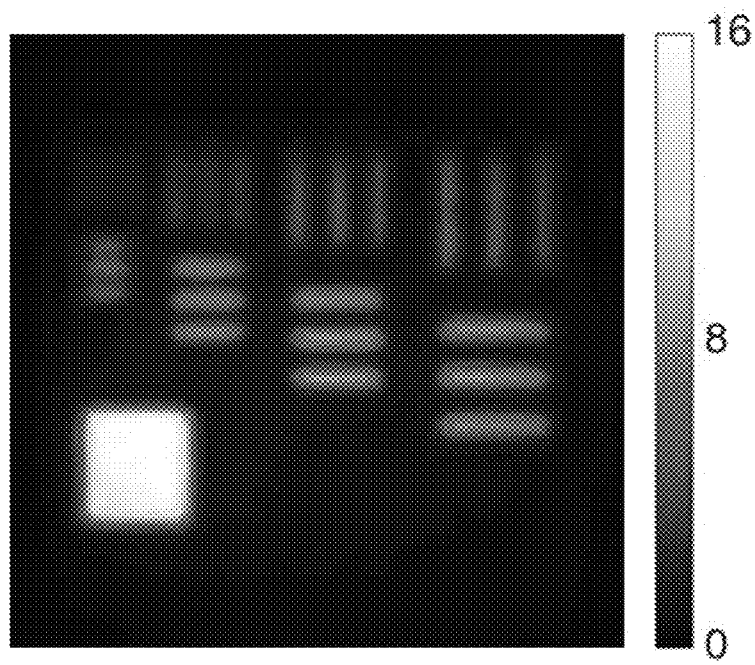

Referring to FIG. 8B, for experiment of a biological tissue, a slice of rat brain tissue is placed on the top of the target in FIG. 8A. A 500 µm-thick slice, whose scattering mean free path was measured to be approximately 100 µm, is used as the brain tissue. As shown in FIG. 8B, same experiment is conducted for biological medium which brings about simultaneously scattering and aberration. As shown in FIGS. 10A and 10B, the images are obtained through the CASS method and the method for imaging according to the present invention, respectively.

Figure 9C:
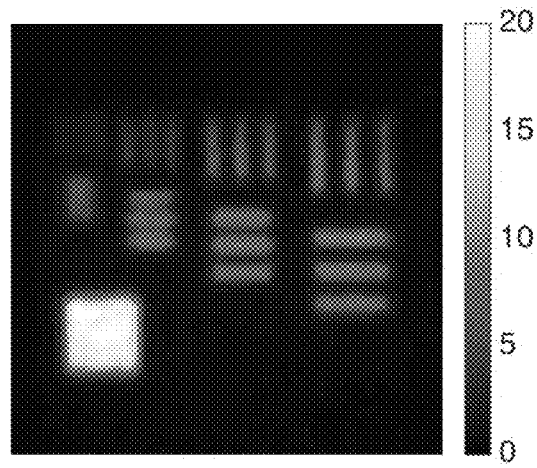

Similar to FIGS. 9A to 9C, for the biological tissue, the method for imaging according to the present invention eliminates scattering and aberration simultaneously, thereby the present invention is capable of imaging of deep depth and high resolution.

In the above mentioned embodiments, as shown in FIG. 5, the aberration of the incidence path is corrected first, and then the aberration of the reflection path is corrected, as an example. On the contrary, the aberration of the incidence path can be corrected after correcting the aberration of the reflection path.

Figure 11:
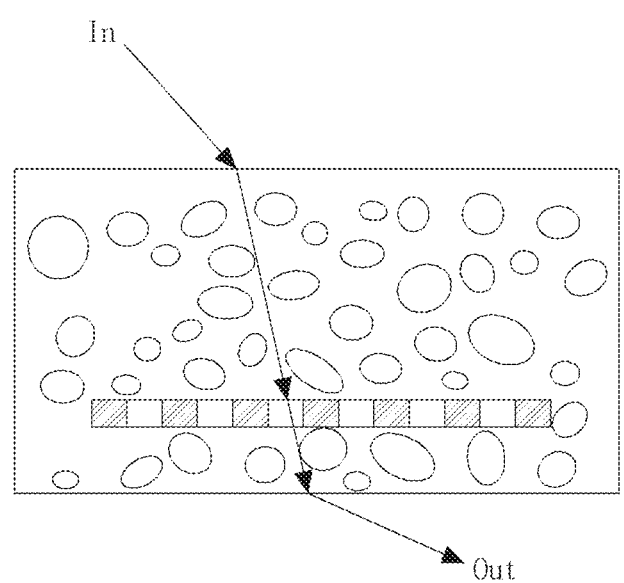
FIG. 11 explains another example to which a method for imaging a target object within media which bring about simultaneously scattering and aberration according to the present invention is applied.

Also, in the above mentioned embodiments, as shown in FIG. 1, the present invention is applied to the reflection beam reflected from the target, as an example. In addition, as shown in FIG. 11, the method for imaging according to the present invention can be applied to the case that the incidence beam penetrates the target object within the media which bring about simultaneously scattering and aberration and a penetration beam is measured.

In this case, it can be explained by replacing the term of 'reflection' in the above mentioned embodiments with the term of 'penetration', and the technical idea of the present invention can be applied to 'penetration' in the same with 'reflection'. In the present invention, the term of 'emission' including meanings of 'reflection' and 'penetration' is used, and the beam from the target object, in which information of the target object is contained, is defined as 'penetration beam'.

It is understood by those skilled in the art that the foregoing description is a preferred embodiment of the disclosed device and that various changes and modifications may be made in the invention without departing from the spirit and scope thereof.

What is claimed is:

1. A method for imaging a target object within media which bring about simultaneously scattering and aberration comprising the following steps:
    (a) obtaining a plurality of emission beams emitted from the target object in accordance with change of an incidence angle of an incidence beam;
    (b) constructing a time-resolved emission matrix which is composed of an incidence wave vector of the incidence beam and an emission wave vector of the emission beam;
    (c) re-constructing the time-resolved emission matrix to an incidence path aberration correction matrix which is composed of the incidence wave vector and a deviation between the emission wave vector and the incidence wave vector;
    (d) applying an incidence path aberration correction set to the incidence path aberration correction matrix, thereby calculating an optimum incidence path aberration correction set at which a total intensity of complex sum of a deviation spectrum between the emission beam and the incidence beam is maximized;
    (e) correcting the time-resolved emission matrix by using optimum incidence path aberration correction set;
    (f) re-constructing the time-resolved emission matrix corrected in the step (e) to a emission path aberration correction matrix which is composed of the emission wave vector and a deviation between the incidence wave vector and the emission wave vector;
    (g) applying an emission path aberration correction set to the emission path aberration correction matrix, thereby calculating an optimum emission path aberration correction set at which a total intensity of complex sum of a deviation spectrum between a reverse emission beam and a reverse incidence beam is maximized, the reverse emission beam and the reverse incidence beam have reverse phase corresponding to the emission path aberration correction matrix;
    (h) correcting the time-resolved emission matrix corrected in the step (e) by using the optimum emission path aberration correction set; and
    (i) obtaining an image by accumulating same deviation spectrum between the emission beam and the incidence beam in the time-resolved emission matrix corrected in the step (h).

2. The method for imaging the target object within media which bring about simultaneously scattering and aberration of claim 1, wherein the step (c) to the step (h) is repetitively executed for the corrected time-resolved emission matrix according to a pre-registered standard; and
    wherein the step (i) is executed after repetitive execution of the step (c) to the step (h).

3. The method for imaging the target object within media which bring about simultaneously scattering and aberration of claim 1, wherein the emission beam comprises a reflection beam reflected from the target object or a penetration beam penetrating the target object.

4. The method for imaging the target object within media which bring about simultaneously scattering and aberration of claim 1, wherein a spectrum of the emission beam to which the incidence path aberration correction set is applied in the step (d) is defined by formula $$\varepsilon_{CLASS}^{(1)}(\Delta\vec{k}) = \sum_{\vec{k}^i} \varepsilon_o(\vec{k}^i + \Delta\vec{k}) e^{i\theta_i^{(1)}(\vec{k}^i)}$$

$$= \sqrt{\gamma}\, O(\Delta\vec{k}) \cdot \sum_{\vec{k}^i} P_i^a(\vec{k}^i) P_o^a(\vec{k}^i + \Delta\vec{k}) e^{i\theta_i^{(1)}(\vec{k}^i)} +$$

$$\sqrt{\beta} \sum_{\vec{k}^i} \varepsilon_o^M(\vec{k}^i + \Delta\vec{k}) e^{i\theta_i^{(1)}(\vec{k}^i)}$$

wherein $\theta_i^{(1)}(\vec{k}^i)$ is the incidence path aberration correction set, $P(\vec{k})$ is a complex pupil function where a subscript 'o' represents an emission path and 'i' represents an incidence path, $\gamma=\exp[-2L/l_s]$, L is a thickness of the media, ls is a scattering mean free path, $\beta$ is an average intensity of a multiple scattering wave in the emission beam, $\vec{k}^i$ is the incidence wave vector, and $\vec{k}^o$ is the emission wave vector which is $\vec{k}^o=\vec{k}^i+\Delta\vec{k}$.

5. The method for imaging the target object within media which bring about simultaneously scattering and aberration of claim 1, wherein the deviation spectrum between the reverse emission beam and the reverse incidence beam to which the emission path aberration correction set is applied in the step (g) is defined by formula $$\varepsilon_{CLASS}^{pc}(\Delta\vec{k}) = \sqrt{\gamma}\, O^{-1}(\Delta\vec{k}) \cdot \sum_{\vec{k}^o} P_o^a(\vec{k}^o)^* P_i^{(1)}(\vec{k}^o + \Delta\vec{k})^* \exp i\theta_o^{(1)}(\vec{k}^o) +$$

$$\sqrt{\beta}\sum_{\vec{k}^o} \varepsilon_o^M(\vec{k}^o + \Delta\vec{k})^* \exp[i\theta_i^{(1)}(\vec{k}^i)]\exp i\theta_0^{(1)}(\vec{k}^o)$$

wherein $\theta_o^{(1)}(\vec{k}^o)$ is the emission path aberration correction set, $P(\vec{k})$ is a complex pupil function where a subscript 'o' represents an emission path and 'i' represents an incidence path, $\gamma=\exp[-2L/l_s]$, $\beta$ is an average intensity of a multiple scattering wave in the emission beam, $\vec{k}^i$ is the incidence wave vector, and $\vec{k}^o$ is the emission wave vector which is $\vec{k}^o=\vec{k}^i+\Delta\vec{k}$.

6. The method for imaging the target object within media which bring about simultaneously scattering and aberration of claim 1, wherein the incidence path aberration correction matrix is re-constructed as type of time-resolved emission matrix after applying the optimum incidence path aberration correction set to the incidence path aberration correction matrix, thereby the time-resolved emission matrix being corrected in the step (e).

7. The method for imaging the target object within media which bring about simultaneously scattering and aberration of claim 1, wherein the emission path correction matrix is re-constructed as type of time-resolved emission matrix after applying the optimum emission path aberration correction set to the emission path correction matrix, thereby the time-resolved emission matrix being corrected in the step (h).

8. The method for imaging the target object within media which bring about simultaneously scattering and aberration of claim 1, wherein a number of random pattern lights with a plurality of incidence angles is incident as the incidence beam.

9. A method for imaging a target object within media which bring about simultaneously scattering and aberration comprising the following steps:
(A) obtaining a plurality of emission beams emitted from the target object in accordance with change of an incidence angle of an incidence beam;
(B) constructing a time-resolved emission matrix which is composed of an incidence wave vector of the incidence beam and an emission wave vector of the emission beam;
(C) re-constructing the time-resolved emission matrix to a emission path aberration correction matrix which is composed of the emission wave vector and a deviation between the incidence wave vector and the emission wave vector;
(D) applying an emission path aberration correction set to the emission path aberration correction matrix, thereby calculating an optimum emission path aberration correction set at which a total intensity of complex sum of a deviation spectrum between a reverse emission beam and a reverse incidence beam is maximized, the reverse emission beam and the reverse incidence beam have reverse phase corresponding to the emission path aberration correction matrix;
(E) correcting the time-resolved emission matrix by using the optimum emission path aberration correction set;
(F) re-constructing the time-resolved emission matrix corrected in the step (E) to an incidence path aberration correction matrix which is composed of the incidence wave vector and a deviation between the emission wave vector and the incidence wave vector;
(G) applying an incidence path aberration correction set to the incidence path aberration correction matrix, thereby calculating an optimum incidence path aberration correction set at which a total intensity of complex sum of a deviation spectrum between the emission beam and the incidence beam is maximized;
(H) correcting the time-resolved emission matrix corrected in the step (E) by using optimum incidence path aberration correction set; and
(I) obtaining an image by accumulating same deviation spectrum between the emission beam and the incidence beam in the time-resolved emission matrix corrected in the step (H).

10. The method for imaging the target object within media which bring about simultaneously scattering and aberration of claim 9, wherein the step (C) to the step (H) is repetitively executed for the corrected time-resolved emission matrix according to a pre-registered standard; and
wherein the step (I) is executed after repetitive execution of the step (C) to the step (H).

11. The method for imaging the target object within media which bring about simultaneously scattering and aberration of claim 9, wherein the emission beam comprises a reflection beam reflected from the target object or a penetration beam penetrating the target object.

12. The method for imaging the target object within media which bring about simultaneously scattering and aberration of claim 9, wherein a spectrum of the emission beam to which the incidence path aberration correction set is applied in the step (G) is defined by formula $$\varepsilon_{CLASS}^{(1)}(\Delta\vec{k}) = \sum_{\vec{k}^i} \varepsilon_o(\vec{k}^i + \Delta\vec{k}) e^{i\theta_i^{(1)}(\vec{k}^i)}$$

$$= \sqrt{\gamma}\, O(\Delta\vec{k}) \cdot \sum_{\vec{k}^i} P_i^a(\vec{k}^i) P_o^a(\vec{k}^i + \Delta\vec{k}) e^{i\theta_i^{(1)}(\vec{k}^i)} +$$

$$\sqrt{\beta}\sum_{\vec{k}^i} \varepsilon_o^M(\vec{k}^i + \Delta\vec{k}) e^{i\theta_i^{(1)}(\vec{k}^i)}$$

wherein $\theta_i^{(1)}(\vec{k}^i)$ is the incidence path aberration correction set, $P(\vec{k})$ is a complex pupil function where a subscript 'o' represents an emission path and 'i' represents an incidence path, $\gamma=\exp[-2L/l_s]$, L is a thickness of the media, ls is a scattering mean free path, $\beta$ is an average intensity of a multiple scattering wave in the emission beam, $\vec{k}^i$ is the incidence wave vector, and $\vec{k}^o$ is the emission wave vector which is $\vec{k}^o=\vec{k}^i+\Delta\vec{k}$.

13. The method for imaging the target object within media which bring about simultaneously scattering and aberration of claim 9, wherein the deviation spectrum between the reverse emission beam and the reverse incidence beam to which the emission path aberration correction set is applied in the step (D) is defined by formula $$\varepsilon_{CLASS}^{pc}(\Delta\vec{k}) = \sqrt{\gamma}\, O^{-1}(\Delta\vec{k}) \cdot \sum_{\vec{k}^o} P_o^s(\vec{k}^o)^* P_i^{(1)}(\vec{k}^o + \Delta\vec{k})^* \exp i\theta_o^{(1)}(\vec{k}^o) +$$

$$\sqrt{\beta} \sum_{\vec{k}^o} \varepsilon_o^M(\vec{k}^o + \Delta\vec{k})^* \exp[i\theta_i^{(1)}(\vec{k}^i)] \exp i\theta_0^{(1)}(\vec{k}^o)$$

wherein $\theta_o^{(1)}(\vec{k}^o)$ is the emission path aberration correction set, $P(\vec{k})$ is a complex pupil function where a subscript 'o' represents an emission path and 'i' represents an incidence path, $\gamma = \exp[-2L/l_s]$, $\beta$ is an average intensity of a multiple scattering wave in the emission beam, $\vec{k}^i$ is the incidence wave vector, and $\vec{k}^o$ is the emission wave vector which is $\vec{k}^o = \vec{k}^i + \Delta\vec{k}$.

14. The method for imaging the target object within media which bring about simultaneously scattering and aberration of claim 9, wherein the incidence path aberration correction matrix is re-constructed as type of time-resolved emission matrix after applying the optimum incidence path aberration correction set to the incidence path aberration correction matrix, thereby the time-resolved emission matrix being corrected in the step (H).

15. The method for imaging the target object within media which bring about simultaneously scattering and aberration of claim 9, wherein the emission path correction matrix is re-constructed as type of time-resolved emission matrix after applying the optimum emission path aberration correction set to the emission path correction matrix, thereby the time-resolved emission matrix being corrected in the step (E).

16. The method for imaging the target object within media which bring about simultaneously scattering and aberration of claim 9, wherein a number of random pattern lights with a plurality of incidence angles is incident as the incidence beam.

* * * * *